United States Patent
Hiejima et al.

[11] Patent Number: 6,139,530
[45] Date of Patent: Oct. 31, 2000

[54] LIQUID MEDICINE INJECTION APPARATUS UTILIZING NEGATIVE PRESSURE

[75] Inventors: Katsuhiro Hiejima; Takeshi Mori, both of Osaka, Japan

[73] Assignee: Nissho Corporation, Osaka, Japan

[21] Appl. No.: 09/273,252

[22] Filed: Mar. 22, 1999

[30] Foreign Application Priority Data

Mar. 27, 1998 [JP] Japan .................................. 10-080875

[51] Int. Cl.⁷ .................................................. A61M 37/00
[52] U.S. Cl. .......................... 604/140; 604/143; 604/218; 604/222
[58] Field of Search .................................... 604/143, 149, 604/152, 187, 218, 222, 228, 140, 141

[56] References Cited

U.S. PATENT DOCUMENTS

| 5,769,824 | 6/1998 | Hjertman et al. | 604/143 |
| 5,807,337 | 9/1998 | Yamada et al. | 604/143 |
| 5,810,778 | 9/1998 | Hjertman et al. | 604/143 |

FOREIGN PATENT DOCUMENTS

WO 92/01484   2/1992   WIPO.
WO 95/28977  11/1995   WIPO.

*Primary Examiner*—John D. Yasko
*Attorney, Agent, or Firm*—Kubovcik & Kubovcik

[57] ABSTRACT

A liquid medicine injection apparatus which is capable of injecting a liquid medicine at an accurate flow rate and which does not require an excessively strong force for filling the apparatus with the liquid medicine. The apparatus includes a barrel 1 provided with a port 11 at the distal end thereof and a shaft 12 extending along the longitudinal axis thereof, a hollow plunger 2 provided at its distal end with a first gasket 3 inserted into the barrel 1 while allowing the shaft 12 of the barrel to pass therethrough, and also provided at the proximal end thereof with a closing member 4 having a vent hole 41; a second gasket 5 connected to the proximal end of the shaft 12; and outside air releasing means 6 for allowing the space between the first and second gaskets to communicate with the outside air. With such an arrangement, a liquid medicine is filled into the barrel 1 due to a negative pressure generated in a third space 25 when the plunger 2 is advanced while the liquid medicine is expelled outside due to a vacuum generated in a second space 24 when the plunger 2 is moved backward.

24 Claims, 6 Drawing Sheets

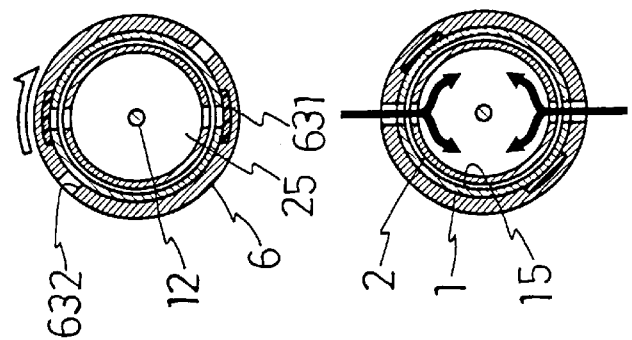
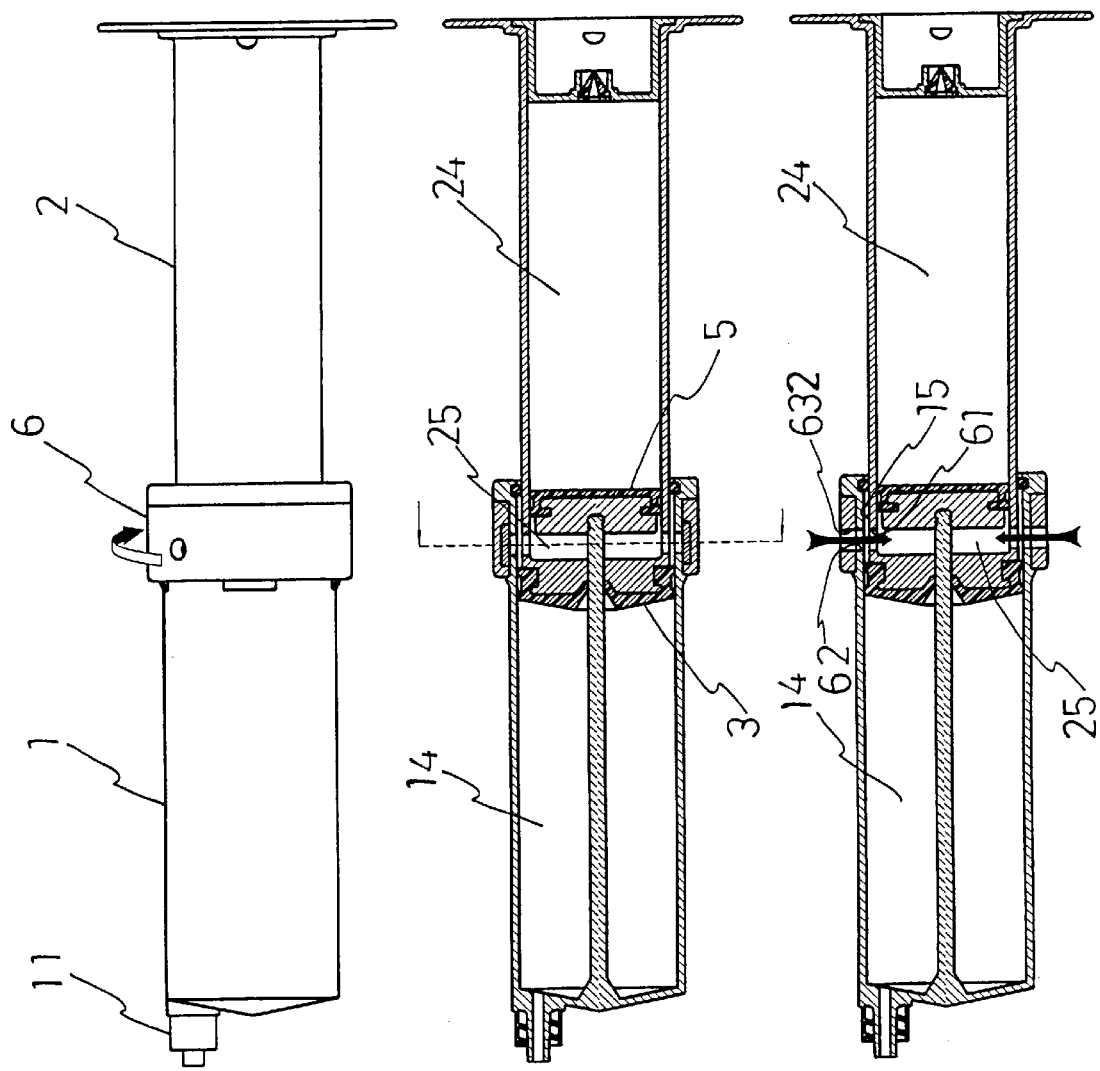
Fig. 4(a)  Fig. 4(b)  Fig. 4(c)

PRIOR ART

LIQUID MEDICINE INJECTION APPARATUS UTILIZING NEGATIVE PRESSURE

BACKGROUND OF THE INVENTION

1. Field of the Invention

The present invention relates to a liquid medicine injection apparatus and more particularly to a liquid medicine injection apparatus that is adapted to inject a liquid medicine into blood vessels, the outside of an epidural space, the subcutaneous tissue, the bladder and the like by making use of a negative pressure.

2. Prior Art

In order to inject a predetermined quantity of liquid medicine into blood vessels and the like, it has been usual to use a syringe pump or a balloon infuser.

However, the syringe pump has the disadvantages that it has a complicated structure and is expensive while the balloon infuser has the disadvantage that since a liquid medicine which fills the balloon is expelled by the contracting force of the expanded balloon which is made of a rubber material, the discharge power is not kept constant.

Therefore, as a means for eliminating such disadvantages, there has been proposed a liquid medicine injection apparatus which is simple in structure and inexpensive and whose medicine discharge power is constant (as disclosed in International Publication No. WO95/28977). As shown in FIG. 6, this apparatus comprises a barrel 130, a first gasket 140 capable of sliding within the barrel 130, a cylinder 210 integrally connected to the barrel 130 and a second gasket 220 slidably and liquid-tightly inserted into the cylinder 210. Further, the first gasket 140 and the second gasket 220 are connected to each other through a plunger 250 so that when barrel 130 is filled with a liquid medicine, the second gasket 220 interlocks with the first gasket 140 to slide within the cylinder 210 thereby reducing the pressure in the cylinder 210.

However, in the case of the above-described liquid medicine injection apparatus, since the first gasket 140 and the second gasket 220 are connected to each other by means of the plunger 250, when the liquid medicine is filled into the barrel 130, the plunger 250 is pulled against the negative pressure in the cylinder 210 and, therefore, a considerable degree of force is required for filling the barrel with the liquid medicine.

SUMMARY OF THE INVENTION

The present invention has been made to overcome the above-described disadvantages and an object of the invention is to provide a liquid medicine injection apparatus which is capable of injecting a liquid medicine at an accurate flow rate and which does not require excessive force for it to be filled with the liquid medicine.

As a result of assiduous studies for solving the problems in the prior art, the present inventors thought of the idea that if the second gasket is inserted into the plunger and if the pressure in the space between the first gasket within the barrel and the second gasket within the plunger could be provided with a negative pressure in advance before the liquid medicine is filled into the barrel, a person would be able to fill the barrel with the liquid medicine with ease by the negative pressure and have completed the present invention on the basis of this idea.

That is, the present invention relates to a liquid medicine injection apparatus which comprises a barrel having a port portion at a distal end thereof and a shaft extending along the longitudinal axis thereof and an opening at a proximal end thereof, a first gasket having a through hole through which said shaft of said barrel can fluid-tightly be inserted and which is fluid-tightly and slidably inserted into said barrel while said shaft of said barrel is passed therethrough, a hollow plunger having a distal end provided with said first gasket and a proximal end closed with a closing member provided with a sealable vent, a second gasket fluid-tightly and slidably inserted into a lumen of the plunger and connected to a proximal end of said shaft of said barrel which is inserted through said through hole of said first gasket so as to project into said plunger; and outside air releasing means for making a space between said first and second gaskets communicate with the outside. The mechanism of the apparatus is such that when said plunger is moved forward, the pressure in the space between said first and second gaskets is reduced; when said plunger is moved backward, the inner space of said barrel is filled with a liquid medicine and at the same time, the space between said second gasket and said closing member is made substantially vacuous; and when the space between said first and second gaskets communicates with the outside by opening said outside air releasing means, said plunger moves forward to expel said liquid medicine to the outside.

In the above-described arrangement, it is preferable for the outside air releasing means to be of a type that comprises a side hole formed in the side wall of said plunger between said first and second gaskets at a position close to said first gasket, a space between the inner wall of said barrel and the outer wall of said plunger, a side hole formed in the side wall of said barrel at a position close to the proximal end of said barrel and a sealing member capable of rotating around an outer surface of said barrel so as to open and close the side hole of said barrel, or of a type that comprises a side hole formed in the side wall of said plunger between said first gasket and said second gasket at a position close to said first gasket, a space between the inner wall of said barrel and the outer wall of said plunger, a vent formed in the side wall of said barrel at a position close to the proximal end of said barrel and a cap removably attached to the vent so as to close the latter.

Further, the vent of the above-described plunger closing member has a check valve which permits the air to go outside. Still further, where the operation of providing a negative pressure in the space between the first and second gaskets by pressing the plunger is performed in such a manner, for example, that the proximal end of the plunger is pressed against a flat desk, an air expelling hole may be formed in the closing member at a position close to the proximal end of the plunger so that the air within the plunger to be expelled through the vent hole of the closing member is allowed to escape therethrough. In addition, a tube provided with flow rate control means may be connected to the port section of the barrel.

BRIEF DESCRIPTION OF THE DRAWINGS

FIG. 4 is a view illustrating how an outside air releasing means of the liquid injection apparatus shown in FIG. 1 is opened.

DETAILED DESCRIPTION OF THE PREFERRED EMBODIMENT

One embodiment of the present invention will now be described with reference to the accompanying drawings.

Figure 1:
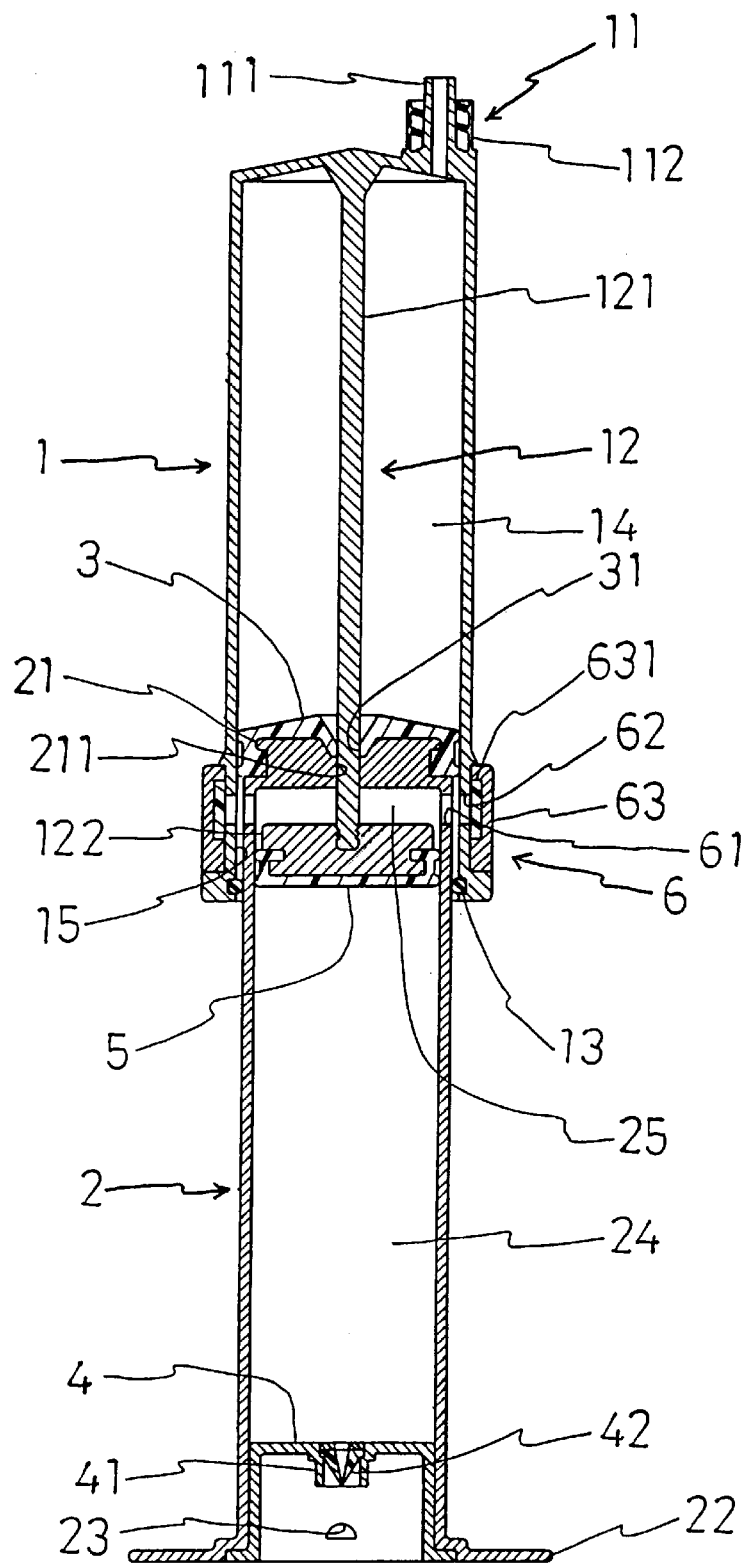
FIG. 1 is a vertical sectional view of a liquid medicine injection apparatus according to one embodiment of the present invention.

As shown in FIG. 1, the liquid medicine injection apparatus according to the present invention comprises a barrel 1, a shaft 12, a hollow plunger 2, a second gasket 5 and outside air releasing means 6.

The barrel 1 is provided with a port 11 at the distal end thereof and the shaft 12 extending along the longitudinal axis thereof. The hollow plunger 2 is provided with a first gasket 3 at the distal end thereof which is inserted into the barrel 1 while the shaft 12 is inserted therethrough. The plunger 2 is closed with a closing member 4 provided with a vent 41 at the proximal end thereof. The second gasket 5 is inserted into the lumen of the plunger 2 and is connected to the proximal end of the shaft 12. The outside air releasing means 6 allows the space between the first gasket 3 and the second gasket 5 communicate with the outside air.

Figure 5:
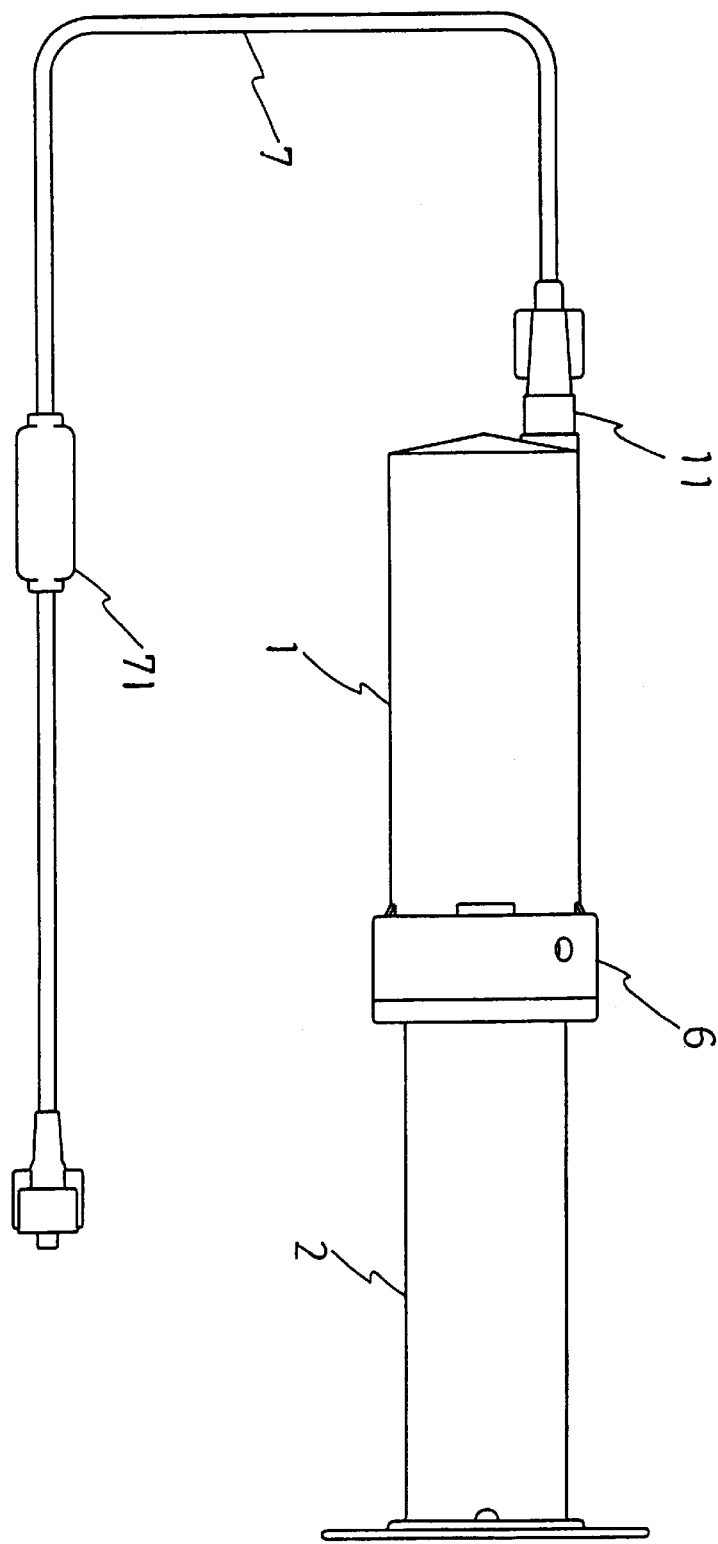
FIG. 5 is a state in which a tube provided with flow rate control means is connected to the liquid medicine injection apparatus shown in FIG. 1.
Figure 6:
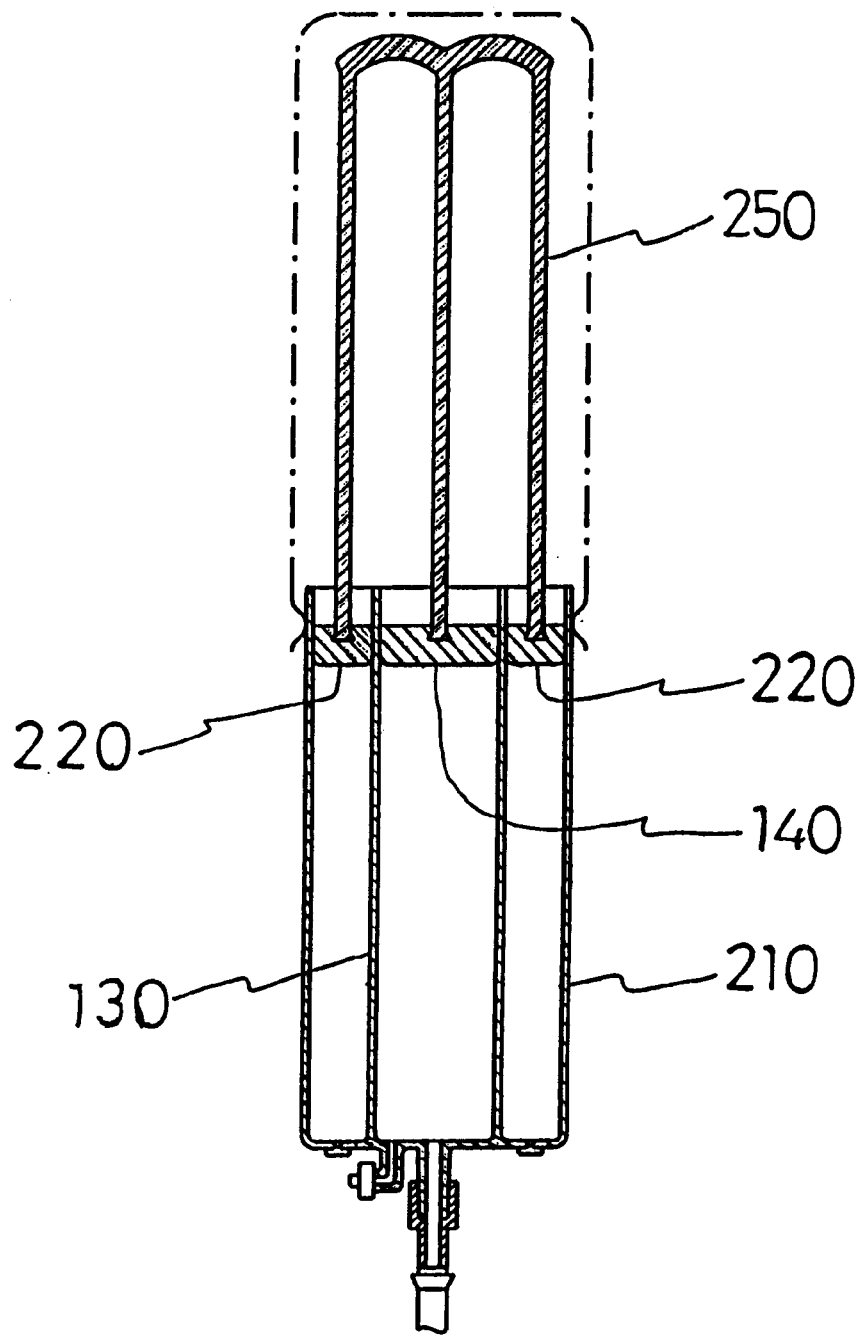
FIG. 6 is a view of one example of a conventional liquid medicine injection apparatus.

The barrel 1 is a cylindrical member made of a plastic material such as polypropylene or polyethylene and having a closed end at the distal end and an open end at the proximal end. Further, the closed distal end of the barrel 1 is provided with the port 11 and the shaft 12 which extends along the longitudinal axis. The port 11 can effect and suck in the liquid medicine and usually comprises a tip 111 and a female coupling means 112 provided concentrically and outside of the tip 111 and with which a catheter (not shown) or the like may be screw-fit. Where necessary, an inlet port and an outlet port may be formed separately instead of as the single port 11. As shown in FIG. 1, the shaft 12 is an axial member which is provided along the longitudinal axis of the barrel 1 in such a manner that it does not close the port 11. The shaft 12 comprises a shank 121 fixed to the distal end of the barrel 1 and a head 122 to which the second gasket 5 is mounted. The tip of the shank 121 is inserted through a through hole 31 of the first gasket 3 of the plunger 2 and a through hole 211 of the head 21 of the plunger 2 and projects into the plunger 2 so as to be coupled to the head 122 of the shaft 12 to which the second gasket 5 is mounted by means of screws. Further, as shown in FIG. 5, a tube 7 provided with flow rate control means 71 may be connected to the port 11.

The plunger 2 is a hollow member made of a plastic material such as polypropylene or polyethylene and has a head 21 to which the first gasket 3 is mounted and a flange 22 at the distal end thereof. The head 21 of the plunger 2 has a through hole 211 through which the shaft 12 can pass. The proximal end of the plunger 2 is closed by the closing member 4 having the vent hole 41 which can be sealed with a cap or a plug (not shown). The first gasket 3 is a sliding member made of an elastic rubber material such as butyl rubber, isoprene rubber, olefin type elastomer or the like and is mounted on the head 21 of the distal end of the plunger 2. Further, the first gasket 3 is provided at the central portion thereof with the through hole 211 through which the shaft 12 of the barrel 1 can fluid-tightly be inserted. The first gasket 3 is fluid-tightly and slidably inserted into the barrel 1 while the shaft 12 is inserted therethrough and through the head 21 of the plunger 2. It should be noted in this connection that the vent hole 41 of the closing member 4 may be provided with a check valve 42 which allows only air to go outside so that the labor of sealing the vent 41 with a cap or the like can be dispensed with. For the check valve 42, it is possible to use, in general, a duck bill type check valve as shown in FIG. 1, a ball type valve or an umbrella type check valve. Further, an air expelling hole 23 may be provided close to the proximal end of the plunger 2 so that when the proximal end of the plunger 2 is blocked, the air expelled from the interior of the plunger 2 through the vent hole 41 is released.

The second gasket 5 is a sliding member made of a rubber material as in the case of the first gasket 3 and it is liquid-tightly and slidably inserted into the plunger 2 while it is mounted on the head 122 of the shaft 12 extending through the first gasket 3.

Figure 2:
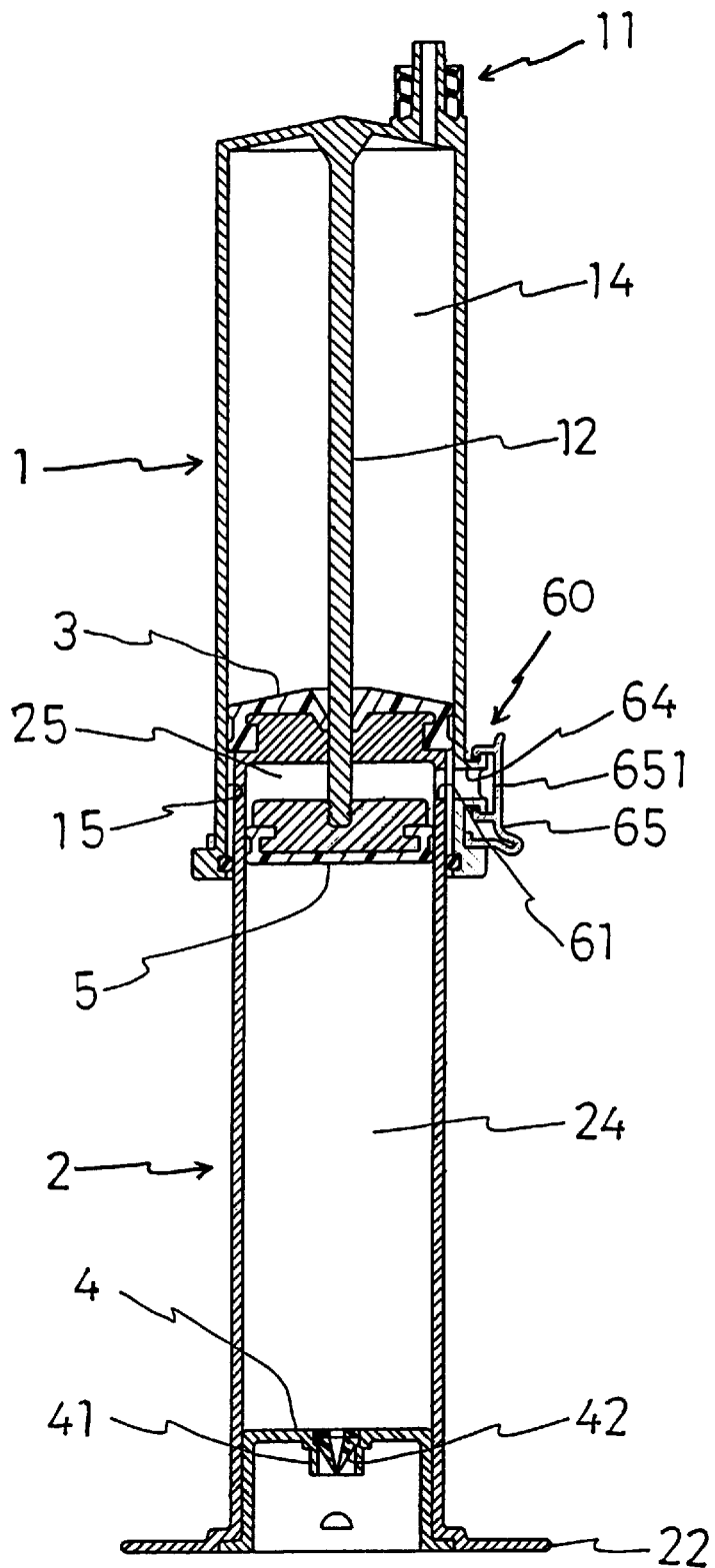
FIG. 2 is a vertical sectional view of a liquid medicine injection apparatus according to another embodiment of the present invention.

The outside air releasing means 6 is a means for allowing the space between the first gasket 3 and the second gasket 5 to communicate with the outside air and the structure shown in FIG. 1 or in FIG. 2 can be employed. The outside air releasing means 6 shown in FIG. 1 comprises a side hole 61 formed in the side wall of the plunger 2 between the first gasket 3 and the second gasket 5 at a position close to the first gasket 3, a space (fourth space) 15 between the inner wall of the barrel 1 and the outer wall of the plunger 2, a side hole 62 formed in the side wall of the barrel 1 at a position close to the proximal end of the barrel 1 and a sealing member 63 capable of opening and closing the side hole 62 of the barrel 1 and rotatable around an outer surface of the barrel 1. In this case, as shown in FIG. 4c, the sealing member 63 is provided with a through hole 632 which communicates with the outside air and a portion 631 which liquid-tightly closes the side hole 62 and is preferably made of an rubber material.

The outside air releasing means 60 shown in FIG. 2 comprises the side hole 61 formed in the side wall of the plunger 2 between the first gasket 3 and the second gasket 5 at a position close to the first gasket 3, the space (fourth space) 15 between the inner wall of the barrel 1 and the outer wall of the plunger 2, a vent 64 formed in the side wall of the barrel 1 at a position close to the proximal end of the barrel 1 and a cap member 65 for detachably closing the vent 64. In order to improve the sealing property of the cap member 65, a sealing member 651 made of an elastic rubber material may be provided inside the top surface of the cap member 65.

The liquid medicine injection apparatus according to the present invention includes therein a total of four spaces as shown in FIGS. 1 and 2. These spaces are a first space 14 surrounded by the inner wall of the barrel 1 and the gasket 3; a second space 24 surrounded by the inner wall of the plunger 2, the closing member 4 and the second gasket 5; a third space 25 surrounded by the inner wall of the plunger 2, the first gasket 3 and the second gasket 5 and a fourth space 15 surrounded by the inner wall of the barrel 1 and the outer wall of the plunger 2. The fourth space 15 is sealed with a sealing member 13. Now, the mechanism of filling and discharge of the liquid medicine will be described by referring to FIGS. 3 and 4.

Figure 3A:
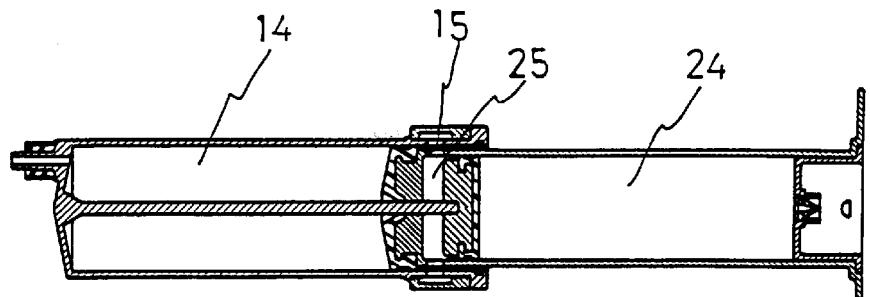
FIG. 3 is an illustrative view showing how a negative pressure is generated in the liquid medicine injection apparatus shown in FIG. 1 through a liquid medicine filling operation.
Figure 3B:
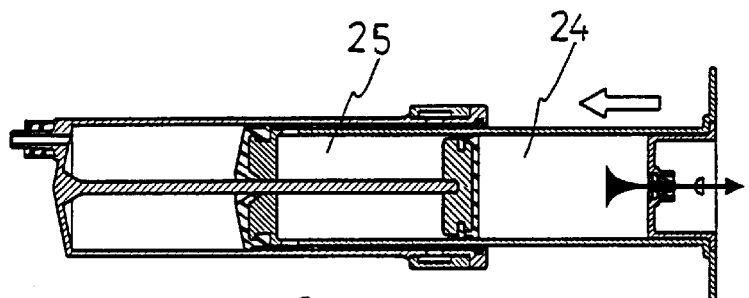
Figure 3C:
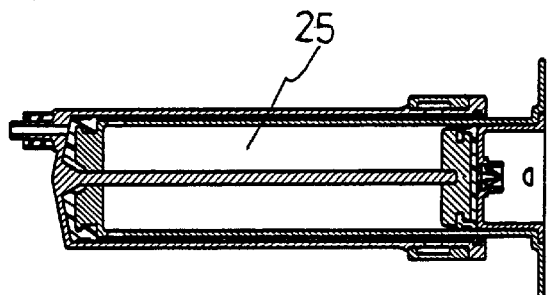
Figure 3D:
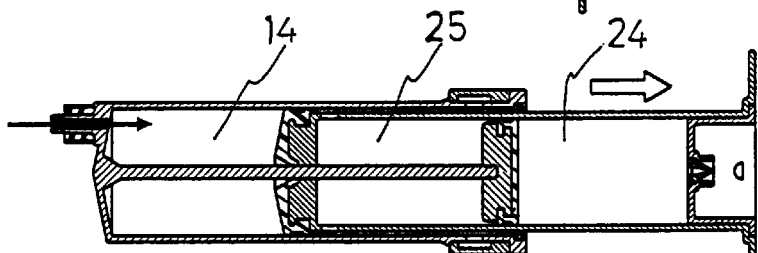
Figure 3E:
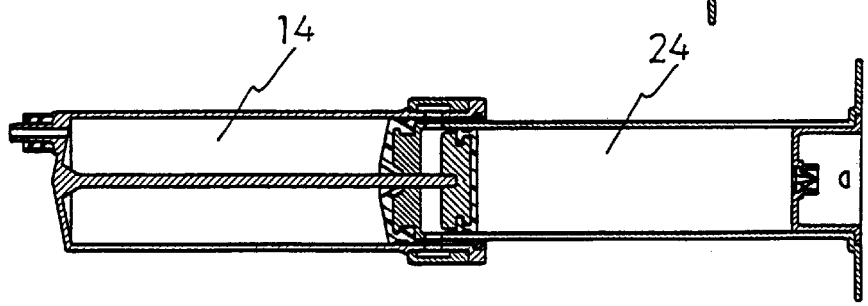

When the plunger 2 is advanced from the state shown in FIG. 3a, almost all the air within the second space 24 is expelled outside through the vent 41, while the third space 25, which is expanded in its sealed state, is brought under a pressure-reduced state (refer to FIGS. 3b and 3c). Next, when the plunger 2 is moved back in the above state, the first space 14 is filled with the liquid medicine. The entry of the outside air into the second space 24 is inhibited by the check valve 42 so that the second space 24 from which almost all the air therein is expelled is expanded under substantially a vacuum state (refer to FIGS. 3d and 3e). In this case, the operation of moving back the plunger 2 can be performed with ease because use can be made of the negative pressure in the third space 25. Next, as shown in FIGS. 4a and 4b, when the third space 25 is made to communicate with the outside air by rotating the outside air releasing means 6 around an outer surface of the barrel 1, the outside air is introduced into the third space 25 from the through hole 632 of the outside air sealing member 63 through the side hole 62, the fourth space 15 and the side hole 61 as shown in FIG. 4c. At this moment, the pressure in the third space 25 becomes equal to the atmospheric pressure so that the first gasket 3 and the head 21 of the plunger 2 are pressed by a force substantially equal to the atmospheric pressure causing the plunger 2 to advance toward the second gasket 5 whereupon the liquid medicine within the first space 14 is automatically expelled by a substantially constant discharge force equal to the atmospheric pressure.

As will be clear from the above-description, the liquid medicine injection apparatus according to the present invention has such various effects that since the liquid medicine is expelled from the apparatus by a negative pressure substantially equal to a vacuum, the injection of the liquid medicine can be performed at an accurate flow rate and since no excessively strong force is required for the filling of the liquid medicine into the apparatus, the burden of the operator is small.

What is claimed is:

1. A liquid medicine injection apparatus which utilizes a negative pressure, which apparatus comprises:
    a barrel having a distal end, a proximal end and a longitudinal axis and having a port portion at said distal end, a shaft extending along said longitudinal axis and an opening at said proximal end;
    a first gasket having a through hole where said shaft of said barrel is fluid-tightly inserted, said gasket being fluid-tightly and slidably inserted into said barrel while said shaft of said barrel passes therethrough;
    a hollow plunger having a lumen, a distal end provided with said first gasket and a proximal end closed with a closing member provided with a sealable vent;
    a second gasket fluid-tightly and slidably inserted into the lumen of the plunger and connected to a proximal end of said shaft of said barrel, said shaft passing through said through hole of said first gasket so as to project into said plunger; and
    outside air releasing means for allowing a space between said first and second gaskets to communicate with the outside,
    wherein when said plunger is moved forward, the pressure in the space between said first and second gaskets is reduced; when said plunger is moved backward, the inner space of said barrel is filled with a liquid medicine and at the same time, the space between said second gasket and said closing member is made substantially vacuous; and when the space between said first and second gaskets thereafter communicates with the outside by opening said outside air releasing means, said plunger moves forward to allow said liquid medicine to be expelled outside.

2. The liquid medicine injection apparatus as described in claim 1, wherein said outside air releasing means comprises a side hole formed in the side wall of said plunger between said first and second gaskets at a position close to said first gasket, a space between the inner wall of said barrel and the outer wall of said plunger, a side hole formed in the side wall of said barrel at a position close to the proximal end of said barrel and a sealing member capable of rotating around an outer surface of said barrel so as to open and close the side hole of said barrel.

3. The liquid medicine injection apparatus as described in claim 1, wherein said outside air releasing means comprises a side hole formed in the side wall of said plunger between said first gasket and said second gasket at a position close to said first gasket, a space between the inner wall of said barrel and the outer wall of said plunger, a vent provided on the side wall of said barrel at a position close to the proximal end of said barrel and a cap removably attached to the vent hole so as to close the latter.

4. The liquid medicine injection apparatus as described in claim 1, wherein said vent hole of said closing member has a check valve which enables the air to be vented outside.

5. The liquid medicine injection apparatus as described in claim 1, wherein an air expelling hole for allowing air to be expelled through said vent of said closing member is provided at a position close to the proximal end of said plunger.

6. The liquid medicine injection apparatus as described in claim 1, wherein a tube having flow rate control means is connected to the port portion of said barrel.

7. The liquid medicine injection apparatus as described in claim 2, wherein said vent hole of said closing member has a check valve which enables the air to be vented outside.

8. The liquid medicine injection apparatus as described in claim 3, wherein said vent hole of said closing member has a check valve which enables the air to be vented outside.

9. The liquid medicine injection apparatus as described in claim 2, wherein an air expelling hole for allowing air to be expelled through said vent of said closing member is provided at a position close to the proximal end of said plunger.

10. The liquid medicine injection apparatus as described in claim 3, wherein an air expelling hole for allowing air to be expelled through said vent of said closing member is provided at a position close to the proximal end of said plunger.

11. The liquid medicine injection apparatus as described in claim 4, wherein an air expelling hole for allowing air to be expelled through said vent of said closing member is provided at a position close to the proximal end of said plunger.

12. The liquid medicine injection apparatus as described in claim 7, wherein an air expelling hole for allowing air to be expelled through said vent of said closing member is provided at a position close to the proximal end of said plunger.

13. The liquid medicine injection apparatus as described in claim 8, wherein an air expelling hole for allowing air to be expelled through said vent of said closing member is provided at a position close to the proximal end of said plunger.

14. The liquid medicine injection apparatus as described in claim 2, wherein a tube having flow rate control means is connected to the port portion of said barrel.

15. The liquid medicine injection apparatus as described in claim 3, wherein a tube having flow rate control means is connected to the port portion of said barrel.

16. The liquid medicine injection apparatus as described in claim 4, wherein a tube having flow rate control means is connected to the port portion of said barrel.

17. The liquid medicine injection apparatus as described in claim 5, wherein a tube having flow rate control means is connected to the port portion of said barrel.

18. The liquid medicine injection apparatus as described in claim 7, wherein a tube having flow rate control means is connected to the port portion of said barrel.

19. The liquid medicine injection apparatus as described in claim 8, wherein a tube having flow rate control means is connected to the port portion of said barrel.

20. The liquid medicine injection apparatus as described in claim 9, wherein a tube having flow rate control means is connected to the port portion of said barrel.

21. The liquid medicine injection apparatus as described in claim 10, wherein a tube having flow rate control means is connected to the port portion of said barrel.

22. The liquid medicine injection apparatus as described in claim 11, wherein a tube having flow rate control means is connected to the port portion of said barrel.

23. The liquid medicine injection apparatus as described in claim 12, wherein a tube having flow rate control means is connected to the port portion of said barrel.

24. The liquid medicine injection apparatus as described in claim 13, wherein a tube having flow rate control means is connected to the port portion of said barrel.

* * * * *